US007930947B2

(12) United States Patent
Counts

(10) Patent No.: US 7,930,947 B2
(45) Date of Patent: Apr. 26, 2011

(54) DRUM PLUG PIERCING AND SAMPLING DEVICE AND METHOD

(75) Inventor: Kevin T. Counts, Aiken, SC (US)

(73) Assignee: Savannah River Nuclear Solutions, LLC, Aiken, SC (US)

( * ) Notice: Subject to any disclaimer, the term of this patent is extended or adjusted under 35 U.S.C. 154(b) by 1008 days.

(21) Appl. No.: 11/296,609

(22) Filed: Dec. 7, 2005

(65) Prior Publication Data
US 2007/0128079 A1    Jun. 7, 2007

(51) Int. Cl.
*G01N 1/00* (2006.01)
(52) U.S. Cl. .............. 73/863.85; 73/863; 73/863.81; 222/80; 222/83; 222/83.5
(58) Field of Classification Search ....... 73/863–863.92; 222/1, 80–91; 30/443, 358–369
See application file for complete search history.

(56) References Cited

U.S. PATENT DOCUMENTS

| | | | | |
|---|---|---|---|---|
| 3,064,768 A | * | 11/1962 | Dotto | 188/370 |
| 5,265,762 A | | 11/1993 | Campbell et al. | |
| 5,349,755 A | * | 9/1994 | Haywood | 30/443 |
| 5,370,268 A | * | 12/1994 | Adams | 222/1 |
| 5,841,038 A | * | 11/1998 | Volz | 73/863.85 |
| 5,988,017 A | | 11/1999 | Franklin et al. | |
| 5,992,475 A | | 11/1999 | Campbell | |
| 6,058,808 A | | 5/2000 | Williams et al. | |
| 6,422,273 B1 | | 7/2002 | Campbell | |
| 6,557,428 B2 | | 5/2003 | Wickland et al. | |
| 6,685,758 B1 | | 2/2004 | Bennett et al. | |
| 6,948,391 B2 | | 9/2005 | Brassell et al. | |

FOREIGN PATENT DOCUMENTS

WO        WO 98/46521        10/1998

OTHER PUBLICATIONS

Nat. Inst. for Occ. Safety and Health, Occ. Safety and Health Guidance Manual for Hazardous Waste Site Activities, publication No. 85-115, Oct. 1985, Ch. 11, Washington DC.

* cited by examiner

*Primary Examiner* — Tony G Soohoo
*Assistant Examiner* — Robert Eom
(74) *Attorney, Agent, or Firm* — J. Bennett Mullinax, LLC

(57) ABSTRACT

An apparatus and method for piercing a drum plug of a drum in order to sample and/or vent gases that may accumulate in a space of the drum is provided. The drum is not damaged and can be reused since the pierced drum plug can be subsequently replaced. The apparatus includes a frame that is configured for engagement with the drum. A cylinder actuated by a fluid is mounted to the frame. A piercer is placed into communication with the cylinder so that actuation of the cylinder causes the piercer to move in a linear direction so that the piercer may puncture the drum plug of the drum.

17 Claims, 4 Drawing Sheets

DRUM PLUG PIERCING AND SAMPLING DEVICE AND METHOD

STATEMENT AS TO RIGHTS TO INVENTIONS MADE UNDER FEDERALLY SPONSORED RESEARCH AND DEVELOPMENT

This invention was made with Government support under Contract No. DE-AC09-96-SR18500 awarded by the United States Department of Energy. The Government has certain rights in the invention.

FIELD OF THE INVENTION

The present invention relates generally to a device and method for the environmental management field. More particularly, the present application involves a drum plug piercing and sampling apparatus that is used to sample contents in the drum by piercing the drum plug so that the drum is not damaged.

BACKGROUND

Stainless steel drums are commonly used for the purpose of storing nuclear waste. Waste is typically positioned inside of a drum so that an empty space is located between the waste and the head of the drum. Hazardous gases may form in this empty space over time due to hydrogen accumulation in the drums. Hydrogen could be produced inside of drums from general corrosion of the drum brought about by storing waste material that includes strong acids. Further, chlorides may cause pitting corrosion in crevices of the drum that may further result in the production of hydrogen. Additionally, radiolysis of water in the drum can produce hydrogen which could pressurize the drum and lead to a flammable atmosphere in the empty space of the drum.

In order to store and ship these drums, the gases inside may need to be sampled and vented. Currently, non-sparking tools are used to pierce drums. These tools allow the gas contents in the drum to be sampled and vented, but breach the drum head and prevent reuse. Drums may also be vented by the use of a filter screwed into the drum head. In this instance, if the drum needs to be sampled the drum vent must be removed or punctured. Such procedures for venting and sampling drums are time consuming and somewhat complex.

Probes with an integral vent and sampling port are also known for use with drums. The probe has a drill bit on one end and is screwed into the drum head and secured thereon. As with other devices, the probe breaches the drum head and prevents it reuse. Additionally, these probes are difficult to remove from the drum as they are screwed into and tightened on the drum head.

Other systems exist for venting and sampling gases in drums in which a filtering port in punched through the drum head at one location while a sampling port is punched through the drum head at a separate location. Installation of these ports results in the depositing of an aluminum bronze tip of the port into the interior of the drum. These tips cannot be retrieved and could potentially contaminate the material stored in the drum.

Accordingly, there remains room for variation and improvement within the art.

SUMMARY

Various features and advantages of the invention will be set forth in part in the following description, or may be obvious from the description, or may be learned from practice of the invention.

The present invention provides for an apparatus and method for piercing a drum plug on a drum in order to sample and vent gases that may accumulate in a space of the drum. The drum is not damaged and can be reused since the pierced drum plug can be subsequently replaced.

In accordance with one exemplary embodiment of the present invention, the apparatus includes a frame that is configured for engagement with the drum. A cylinder that is actuated by a fluid is mounted to the frame. A piercer is placed into communication with the cylinder so that actuation of the cylinder causes the piercer to move in a linear direction so that the piercer may puncture the drum plug of the drum.

The present invention also provides for an apparatus as immediately discussed in which a collection tube is present that surrounds at least a portion of the piercer when the cylinder is in an unactuated state. The collection tube has a collection tube port that is in fluid communication with an opening on one end of the collection tube through an interior of the collection tube. Gases from the drum may be transported through the collection tube for sampling and/or venting. In accordance with another exemplary embodiment, a collection canister for receiving and storing gases from the drum is present and is in fluid communication with the collection tube port through a collection line.

Also provided in accordance with one exemplary embodiment is an apparatus as previously discussed in which the piercer has a slot. The slot, opening of the collection tube, interior of the collection tube, and the collection tube port define a passageway for the transport of gases.

One aspect of the present invention provides for an apparatus for the piercing of a drum plug of a drum that includes a frame configured for engaging the drum. A cylinder is mounted to the frame and is configured for being actuated by a fluid. A piercer is in communication with the cylinder so that actuation of the cylinder causes the piercer to move. The piercer is configured for puncturing the drum plug of the drum. A collection tube is present and is urged towards the drum plug during actuation of the cylinder. The collection tube defines a passageway for the transport of gases from the drum. The collection tube is configured to remain on one side of the drum plug during puncturing of the drum plug by the piercer.

In accordance with yet another aspect of the invention, the collection tube of the apparatus as immediately discussed surrounds at least a portion of the piercer when the cylinder is unactuated. Additionally, the collection tube defines a collection tube port. In a further aspect of the invention, the apparatus as immediately discussed has a collection canister in fluid communication with the collection tube port through a collection line. The collection canister is configured for receiving and storing gases present in the drum for testing.

An additional aspect of the present invention includes an apparatus as discussed above in which a ram is attached to both the cylinder and the piercer so that actuation of the cylinder urges the ram towards the collection tube. An additional aspect exists in an apparatus as immediately discussed in which a stack of disc springs are positioned between the cylinder and the collection tube. Actuation of the cylinder causes compression of the disc springs. The disc springs act to absorb force exerted by the cylinder and act to regulate the amount of force imparted to the collection tube.

Another aspect of the present invention involves an apparatus as discussed above in which a nylon washer is located at an end of the collection tube. The nylon washer forms a seal against the drum plug when the cylinder is actuated to urge the collection tube towards the drum plug during puncturing of the drum plug. The nylon washer is unsealed against the drum plug to allow gas in the drum to vent when force provided by the cylinder is relieved after puncturing of the drum plug.

Other aspects of the present invention are provided in an apparatus as discussed above in which the cylinder is a hydraulic cylinder and the fluid is hydraulic fluid.

The present invention also provides for a method of piercing a drum plug of a drum and collecting a gas sample therefrom. The method includes the step of attaching a frame to the drum so that a collection tube and a piercer carried by the frame are positioned over the drum plug. The method also includes the step of actuating a cylinder so that the piercer is driven linearly through the drum plug of the drum and so that the collection tube is urged against the exterior of the drum plug and forms a seal. Gas from the drum is collected into a collection canister that is in fluid communication with the drum through a collection tube and a collection line configured with the collection tube.

In accordance with another aspect of the present invention, the method as immediately discussed includes the step of venting the drum. Venting may occur when force on the collection tube from the cylinder is reduced so that the collection tube becomes unsealed with the drum plug.

Another exemplary embodiment of the present invention exists in a method as discussed above that includes the step of compressing a stack of disc springs that are positioned between the cylinder and the collection tube.

These and other features, aspects and advantages of the present invention will become better understood with reference to the following description and appended claims. The accompanying drawings, which are incorporated in and constitute part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended Figs. in which.

Figure 1:
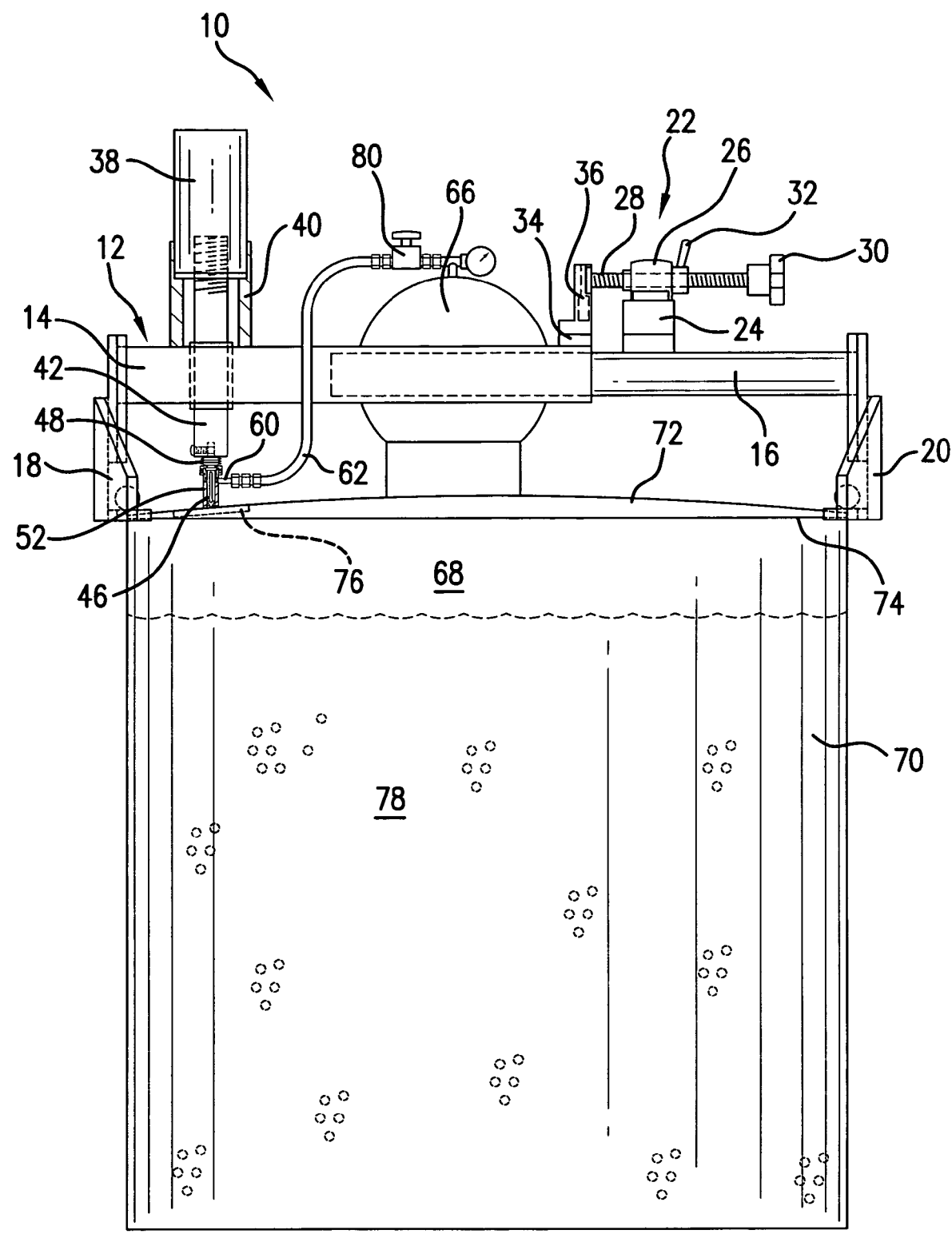
FIG. 1 is an elevation view of a drum plug piercing and sampling device located on a drum in accordance with one exemplary embodiment of the present invention.

Repeat use of reference characters in the present specification and drawings is intended to represent the same or analogous features or elements of the invention.

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to about 7 also includes a limit of up to about 5, up to about 3, and up to about 4.5.

The present invention provides for a drum plug piercing and sampling device 10 and method that may be used to pierce and sample drums 70 that contain waste material 78. The device 10 is configured to pierce a drum plug 76 of the drum 70 so that the drum 70 remains undamaged and can be reused. In this regard, the drum plug 76 can be unscrewed and replaced while the rest of the drum head 72 is not damaged. The device 10 includes a hydraulic cylinder 38 that drives a piercer 46 through the drum plug 76. A collection tube 52 that may surround the piercer 46 has a collection line port 60 through which gas in the drum 70 may be acquired by a collection canister 66 for sampling. Hydraulic pressure may be relieved in order to allow the piercer 46 to be withdrawn from the drum 70 so that gases in the drum 70 can be vented.

One exemplary embodiment of the device 10 is shown in FIG. 1. Here, the device 10 has a frame 12 that includes a larger slider tube 14 that receives a smaller slider tube 16. The slider tubes 14 and 16 slide relative to one another so that the length of the frame 12 may be adjusted. Although shown as having square cross-sections, the slider tubes 14 and 16 may be variously configured in accordance with other exemplary embodiments. A first grip 18 is attached to slider tube 14 and a second grip 20 is attached to slider tube 16. The grips 18 and 20 are configured for engaging and gripping a drum rim 74 of a drum 70. The device 10 can be used on various types of drums 70. For example, the drum 70 may be a 55 gallon drum in accordance with one exemplary embodiment. As shown, the grips 18 and 20 are rigidly attached to the larger slider tube 14 and smaller slider tube 16 and do not pivot therewith. However, the grips 18 and 20 could be designed to pivot in accordance with other exemplary embodiments. Grips 18 and 20 are known in the art and may be provided, for example, as those found in a 92 series drum lifter manufactured by Morse Mfg. Co., Inc. located at 727 West Manlius St., P.O. Box 518, E. Syracuse, N.Y. 13057 USA.

A clamp 22 is attached to the frame 12 and is used to urge the frame 12 against the drum 70 to hold the device 10 in place. The clamp 22 may be an FRL series De-Sta-Co® clamp in accordance with one exemplary embodiment that is provided by De-Sta-Co Industries, 31791 Sherman Drive, Madison Heights, Mich. 48071 USA. A base 24 is mounted onto the smaller slider tube 16 and in turn has a housing 26 of clamp 22 mounted thereon. A clamp member 36 is mounted onto a base 34 that is in turn mounted on the larger slider tube 14. A spindle bar 28 of the clamp 22 is disposed through the housing 26 and interacts with the clamp member 36. The spindle bar 28 may be permanently fixed to the clamp member 36 or may be configured to move into and out of engagement with the clamp member 36 in accordance with various exemplary embodiments. When attached to the clamp member 36, a user may slide the spindle bar 28 linearly in order to adjust the relative positions of the slider tubes 14 and 16 of frame 12.

The clamp 22 is provided with a locking lever 32 that can be turned by the user in order to engage a locking mechanism and hence lock the position of the spindle bar 28 with respect to the housing 26. The locking lever 32 may be actuated once the slider tubes 14 and 16 are properly positioned so that the grips 18 and 20 adequately grip the drum rim 74 to hold frame 12 onto drum 70. The clamp 22 also includes a knob handle 30 that can be turned by the user in order to "fine" adjust the clamping force of the clamp 22. The locking lever 32 may be turned by the user in order to release the clamping force once the piercing and sampling operation is completed. Although shown as a clamp 22, it is to be understood that various mechanisms may be employed in order to secure the positioning of slider tubes 14 and 16. For example, a set screw may be used to fix the relative position of the slider tubes 14 and 16. Alternatively, a series of holes may be made along the length of the slider tubes 14 and 16 and a bar may be inserted through aligned holes when the slider tubes 14 and 16 are adjusted to a desired position. Although described as an adjustable frame 12, it is to be understood that the frame 12 need not be adjustable in accordance with various exemplary embodiments.

In order to pierce a drum plug 76 of the drum 70, the device 10 may employ a hydraulic cylinder 38 that is mounted onto the larger slider tube 14 by way of a cylinder connector 40. The cylinder connector 40 can be welded or mechanically attached to the larger slider tube 14. The hydraulic cylinder 38 may be received by the cylinder connector 40 and held thereto by way of a press fit. Additionally or alternatively, mechanical fasteners may be used in order to attach these two components as is commonly known in the art.

The hydraulic cylinder 38 may be any type of cylinder capable of providing the required linear movement and force needed to pierce the drum plug 76. For example, the hydraulic cylinder 38 is in one exemplary embodiment an Enerpac® RC102 hydraulic cylinder manufactured by Enerpac located at 6100 N. Baker Rd., Milwaukee, Wis. 53209 USA. This type of cylinder is single acting and has a capacity of 10 tons and a $2\frac{1}{8}^{th}$ inch stroke. In accordance with other exemplary embodiments, the capacity of the hydraulic cylinder 38 is from 5 to 100 tons and may have a stroke of up to 14.25 inches. Although described as being a hydraulic cylinder 38, it is to be understood that the cylinder 38 need not be hydraulically actuated in accordance with various exemplary embodiments. For example, the cylinder 38 may be a pneumatic cylinder or may in fact be a mechanically driven component in other embodiments.

Figure 2:
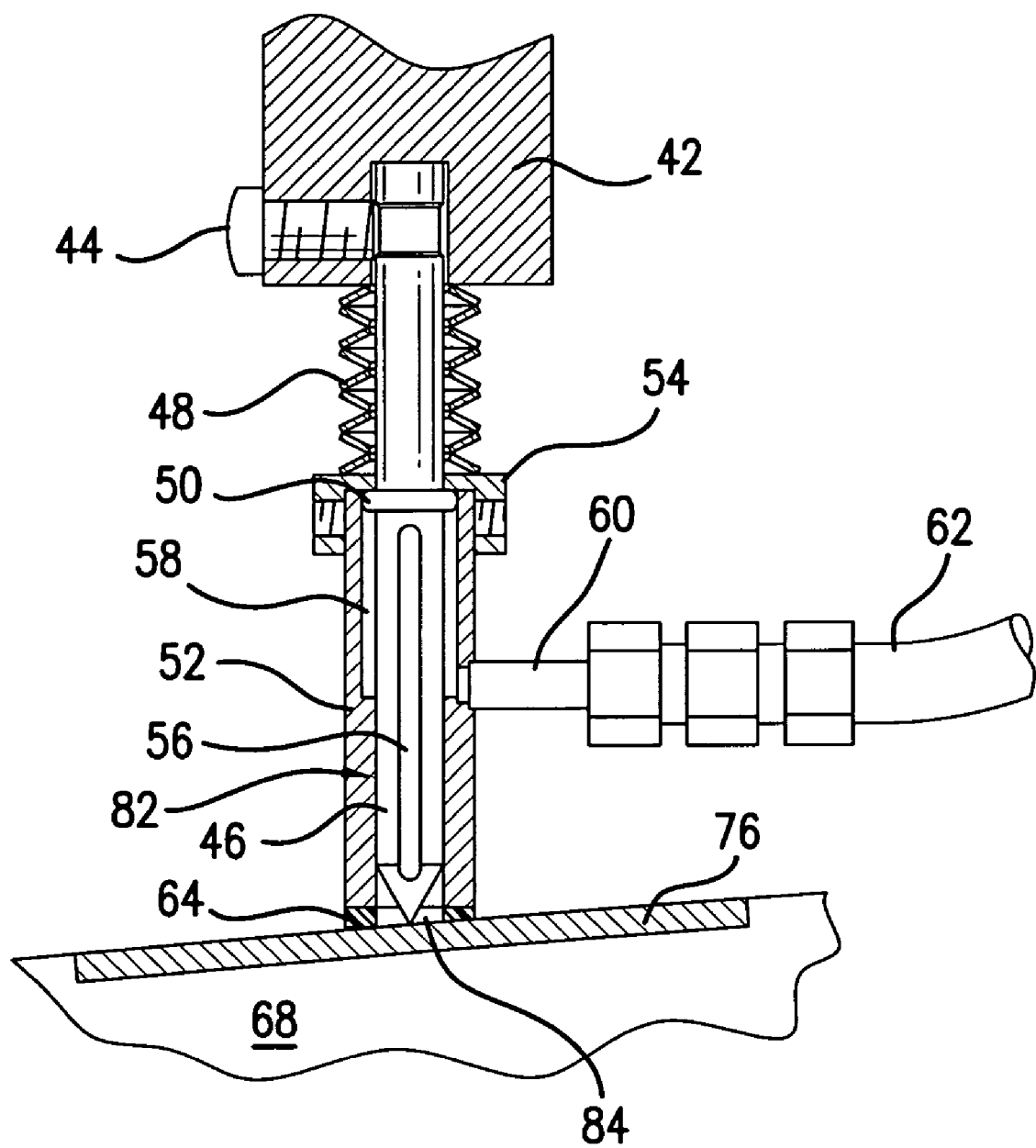
FIG. 2 is a detailed elevation view of the piercer and associated components of the device of FIG. 1 shown in an unactuated position.

A ram 42 is attached to the hydraulic cylinder 38 and moves in response to actuation thereof. The ram 42 may be screwed into the hydraulic cylinder 38 or may be attached in any known manner. As shown in better detail in FIG. 2, a piercer 46 is held onto the ram 42 by way of a set screw 44. The set screw 44 can be loosened to allow for removal of a contaminated piercer 46 and collection tube 52. Contaminated components can then be appropriately stored while the rest of the device 10 is stored elsewhere as a clean unit.

The piercer 46 is provided in order to be driven through the drum plug 76 to vent the drum 70 and allow sampling of gases therein. The piercer 46 may be made of a variety of materials. For example, the piercer 46 can be a copper alloy or may be composed of aluminum, nickel, and bronze in certain exemplary embodiments. The piercer 46 may be made of non-sparking Ampco® 45 distributed by Atlas Bronze located at 445 Bunting Ave., Trenton, N.J. 08611 USA. Desirably, the piercer 46 may be made of a material that reduces the occurrence of sparks so that contact with the drum plug 76 does not cause sparking which could result in an explosion if explosive gases are present in the drum 70. The drum plug 76 may have a thickness of 2 inches in accordance with one exemplary embodiment. In other embodiments, the piercer 46 is configured to pierce drum plugs 76 that can range anywhere from $\frac{1}{4}^{th}$ to 5 inches in thickness. The piercer 46 can be sized and constructed to pierce drum plugs 76 based on their size and construction.

A collection tube 52 that has a collection tube cap 54 surrounds a portion of the piercer 46 when the piercer 46 is in the unactuated position. A plurality of Belleville disc springs 48 are disposed between the ram 42 and the collection tube cap 54 of the collection tube 52. The Belleville disc springs 48 used may be made of high-carbon with a 0.317 inch inner diameter, a 0.625 inch outer diameter, and 0.022 inches in thickness and may be supplied by McMaster-Carr® having a mailing address of P.O. Box 740100, Atlanta, Ga. 30374-0100 USA. The Belleville disc springs 48 may be provided in any number and may be stacked in a variety of configurations. As shown, the Belleville disc springs 48 are stacked in an inverted manner to increase the deflection of the spring by the number of springs in the stack while retaining the load of only one across the span of the stack. In alternative exemplary embodiments, the Belleville disc springs 48 may be stacked in a parallel manner or may be stacked in both a parallel and inverted manner to increase both the load and deflection. Although shown as employing Belleville disc springs 48, other types of springs or dampers may be used in other embodiments.

A nylon washer 64 is positioned at an end of the collection tube 52 opposite the collection tube cap 54. One nylon washer 64 that may be selected for use in the device 10 is offered by Cannon Gasket Inc., located at 287 Industry Way, Upland, Calif. 91786 USA. The nylon washer 64 is located between the collection tube 52 and the drum plug 76. Force transmitted from the ram 42 is transferred to the nylon washer 64 through the Belleville disc springs 48. The Belleville disc springs 48 act to regulate the amount of load on the nylon washer 64 so that the nylon washer 64 may correctly seal against the drum plug 76. Although described as employing both the Belleville disc springs 48 and the nylon washer 64, it is to be understood that these components are not present in other exemplary embodiments. Also, other members capable of effecting a seal against the drum plug 76 can be used instead of a nylon washer 64 such as a rubber gasket.

Figure 3:
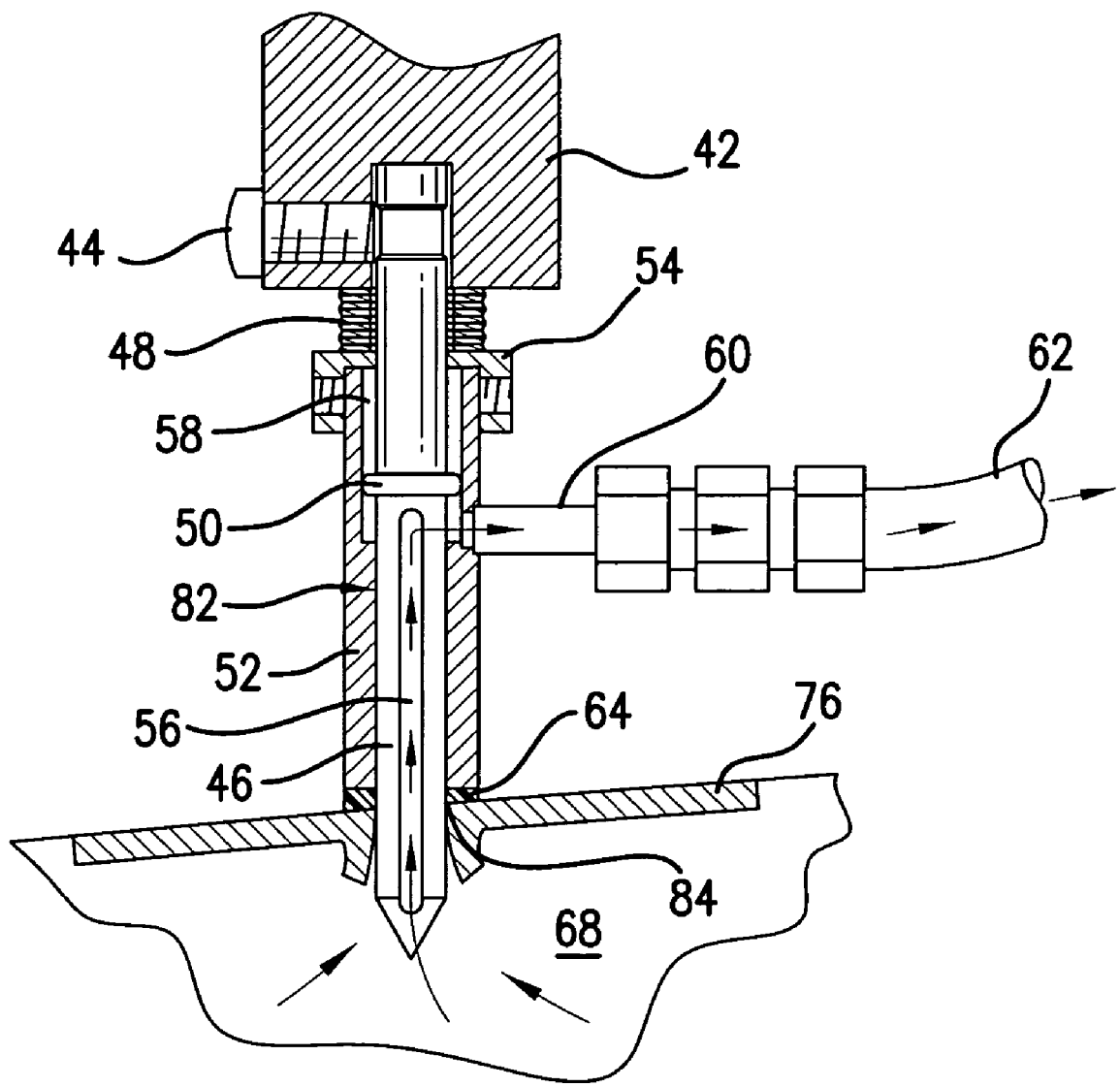
FIG. 3 is a detailed elevation view of the piercer and associated components of the device of FIG. 1 shown in an actuated position.

FIG. 3 shows the actuated position of the piercer 46. Here, the hydraulic cylinder 38 is actuated causing ram 42 to move downwards and hence compress the Belleville disc springs 48. The piercer 46 is disposed through the Belleville disc springs 48 and is connected to the ram 42. The piercer 46 moves downward in response to movement by the ram 42 and penetrates the drum plug 76 to access a space 68 of the drum 70 present between waste 78 (FIG. 1) and drum head 72. Downward movement of the ram 42 also acts to compress the nylon washer 64 against the drum plug 76 to create the aforementioned seal. Movement of the piercer 46 may be linear only such that the piercer 46 does not rotate to pierce the drum plug 76 but instead punches through the drum plug 76 with just a linear movement.

Figure 4:
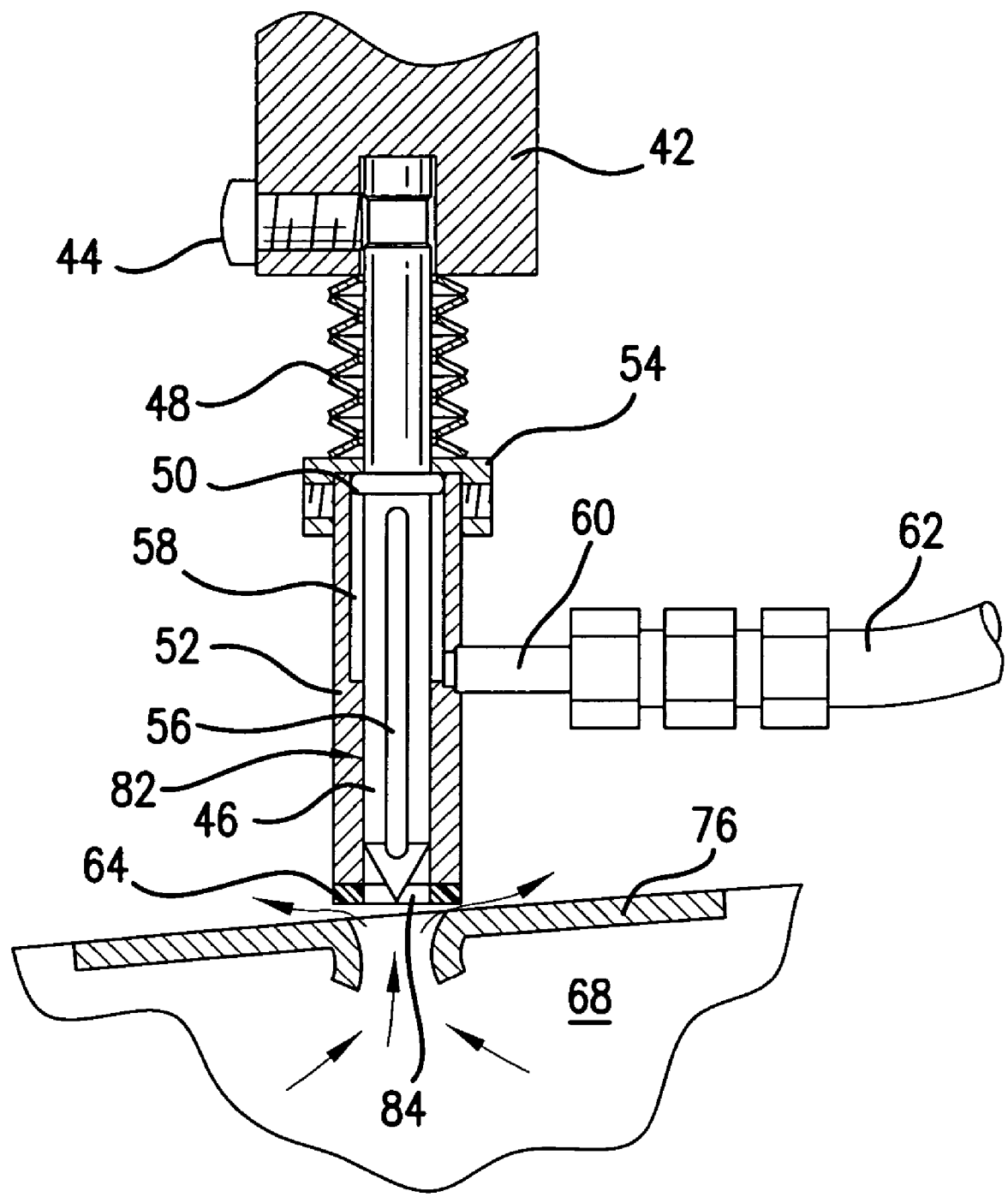
FIG. 4 is a detailed elevation view of the piercer and associated components of the device of FIG. 1 shown withdrawn from the interior of the drum after puncturing the drum plug.

The device 10 can be designed so that the piercer 46 is the only portion of the device 10 that enters the interior of drum 70. As shown in FIG. 4, the collection tube 52 and associated components remain on the exterior of drum 70. The piercer 46 is likewise withdrawn from the interior of drum 70 upon release of hydraulic pressure without further damaging the drum plug 76.

The interior 82 of the collection tube 52 defines a passageway through which gases may be transported. Gases present in the drum 70 can be evacuated from the space 68 by going through an axial opening 84 of the collection tube 52 and into an enlarged bore portion 58 of the collection tube 52. One or more slots 56 defined on the piercer 46 allow for gases to be transported through the collection tube 52. In accordance with one embodiment, the piercer 46 is a solid member that has one slot 56 defined thereon. As such, the piercer 46 does not have an axial bore in accordance with various exemplary embodiments but instead has a solid center to provide strength for piercing the drum plug 76. The piercer 46 can be configured in any suitable manner. For example, the piercer 46 is elongated with a generally cylindrical cross-section having a conical tip in accordance with one embodiment.

As shown, gases may escape the space 68 through an axial opening 84 on one end of the collection tube 52. In this regard, the collection tube 52 remains on the outside of drum 70 and, as shown in one exemplary embodiment, has a single axial opening 84 for the collection of gases from space 68. An O-ring 50 is attached to the piercer 46 and creates a seal in the collection tube 52 to prevent gases from escaping the collection tube 52 through the top of the collection tube cap 54. A collection line 62 is placed into communication with the interior 82 of the collection tube 52 through a collection line port 60. The collection line port 60 may be a $\frac{1}{8}^{th}$ inch male pipe fitting in accordance with one exemplary embodiment. A pathway is thus created from the space 68 through the collection tube 52 and into the collection line 62. The collection tube 52 may be provided in any shape. For example, the collection tube 52 may have a generally cylindrical, square, or rectangular cross-section in accordance with various exemplary embodiments.

As shown in FIG. 1, the collection line 62 feeds a collection canister 66. The collection canister 66 may have a vacuum formed therein in order to pull gases from the space 68 through the collection tube 52 and collection line 62. The vacuum strength may have a value of −30 inches of Hg in accordance with one exemplary embodiment. The collection canister 66 can then be transported to a separate location for testing of the gases collected therein. The collection canister 66 is generally made of a rugged construction and is typically made of an inert material that will not react with the collected gases. Any type of collection canister 66 may be used. For example, in accordance with one exemplary embodiment, the collection canister 66 is a six liter Silcocan Canister manufactured by Restek Corporation® having a mailing address of 110 Benner Circle, Bellefonte, Pa. 16823 USA.

FIG. 4 shows various components of the device 10 after the removal of hydraulic force to the hydraulic cylinder 38. A return spring in the hydraulic cylinder 38 causes the piercer 46 to be withdrawn from the space 68. As pressure on the nylon washer 64 is relieved, gases present in the drum 70 can vent between the nylon washer 64 and the drum plug 76. It is to be understood, however, that the device 10 may allow for venting of gases from the drum 70 at other locations. For example, gases may be vented from the collection line port 60 or out of the collection canister 66.

In order to operate the device 10 so that gases may be sampled and vented from the drum 70, the device 10 is positioned with respect to the drum 70 so that the piercer 46 is located above the drum plug 76. In accordance with one exemplary embodiment, the drum plug 76 is located between the rim of the drum plug 76 and a center stiffener of the drum plug 76. However, the piercer 46 may be positioned to pierce any portion of the drum plug 76 in accordance with other exemplary embodiments. The clamp 22 is tightened so that the slider tubes 14 and 16 are pulled thus causing the grips 18 and 20 to tighten against the drum 70 to secure the device 10. The grips 18 and 20 may be urged against the drum rim 74 or other portion of the drum head 72 or drum 70.

The nylon washer 64 may be positioned between the collection tube 52 and the drum plug 76. The nylon washer 64 may be connected to an end of the collection tube 52 or may be a separate piece that is positioned at the proper location by the user. If not all ready performed, the collection line 62 is attached to the collection line port 60 to allow gases to be collected by the collection canister 66. A vent associated with the collection canister 66 or with the collection line 62 may be used to vent gases as desired. In alternative exemplary embodiments, the collection line 62 is not attached to the collection line port 60 thus allowing gases in the collection tube 52 to vent without being sampled.

Once the device 10 is properly positioned, the drum 70 may be isolated from personnel and hydraulic pressure may be supplied to the hydraulic cylinder 38. Actuation of the hydraulic cylinder 38 causes the ram 42 to move downwards thus compressing the Belleville disc springs 48. Pressure may be supplied to or increased on the hydraulic cylinder 38 until the Belleville disc springs 48 are completely compressed. The piercer 46 will move downwards due to its attachment to the ram 42 and penetrate the drum plug 76 in a location between the rim of the drum plug 76 and the center stiffener of the drum plug 76 and access the space 68 of the drum 70. A valve 80 associated with the collection canister 66 can be opened to allow gases in the space 68 to be drawn into the collection canister 66 for sampling. The valve 80 may be closed once the pressure of the collection canister 66 and the drum 70 are at equilibrium.

Next, hydraulic pressure may be relieved in order to allow the return spring in the hydraulic cylinder 38 to cause the piercer 46 to be withdrawn from inside the drum 70. The piercer 46 may be removed from the interior of drum 70 so that no portion of the piercer 46 is deposited or remains therein. Upward movement of the ram 42 and the piercer 46 allows the drum 70 to vent. Venting may be effected due to decreased pressure on the nylon washer 64 thus allowing venting of gases at the location of the nylon washer 64 and drum plug 76.

The collection canister 66 may be disconnected from the collection line 62 and transported to a remote location, if desired, for testing of the collected gases. The clamp 22 can then be loosened to allow the device 10 to be removed from the drum 70. The pierced drum plug 76 may be unscrewed and replaced with a new drum plug 76 to seal the drum 70 and allow for further storage. The drum 70 is not damaged during this procedure and can remain in use once the drum plug 76 is replaced. As described, the drum plug 76 is the only portion of the drum 70 that is pierced. As such, the device 10 can be configured to allow for remote piercing of the drum 70, reuse of the drum 70 after sampling and/or venting, and does not introduce contamination to the drum 70 or materials stored therein.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed:

1. An apparatus for piercing a drum plug of a drum, comprising:
   a frame configured for engagement with a drum;
   a cylinder mounted to said frame, said cylinder configured for actuation by a fluid;

a collection tube surrounding at least portion of a piercer when said cylinder is in an unactuated state, said collection tube defining an interior, a collection tube port, and an opening on one end, said collection tube port being in fluid communication with said opening through said interior, said piercer further defining a slot on an exterior surface of said piercer such that said slot is in fluid communication with said interior of said collection tube, wherein said piercer has a solid center, and wherein said exterior surface onto which said slot is defined directly faces an interior wall of said collection tube when said cylinder is in the unactuated state;

said piercer in communication with said cylinder such that actuation of said cylinder causes said piercer to move in a linear direction, wherein said piercer is configured for puncturing the drum plug of the drum;

a collection line port attached to said collection tube and in fluid communication with said interior through said collection tube port, wherein the position of said collection line port remains stationary with respect to said collection tube and the drum plug during movement of said piercer in the linear direction when puncturing the drum plug of the drum, wherein contents of the drum are moved through the collection line port; and a collection line attached to said collection tube by way of said collection line port, wherein the position of said collection line remains stationary with respect to said collection tube and the drum plug during movement of said piercer through the drum plug of the drum, and wherein contents of the drum are moved through the collection tube.

2. The apparatus as in claim 1, further comprising a collection canister in fluid communication with said collection line port through said collection line, said collection canister configured for receiving and storing gases for testing.

3. The apparatus as in claim 1, further comprising:
a ram attached to said cylinder, wherein said piercer is attached to said ram; and a stack of disc springs positioned between said ram and said collection tube, wherein said piercer is disposed through said stack of disc springs, and wherein actuation of said cylinder causes said ram to compress said disc springs and urge said collection tube towards the drum plug during puncturing of the drum plug.

4. The apparatus as in claim 1, further comprising a nylon washer located on an end of said collection tube, wherein said nylon washer forms a seal against the drum plug when said cylinder is actuated to urge said collection tube towards the drum plug during puncturing of the drum plug, and wherein said nylon washer allows gases to vent from the drum when force provided by said cylinder is relieved after puncturing of the drum plug.

5. The apparatus as in claim 1, wherein said cylinder is a hydraulic cylinder and wherein said fluid is a hydraulic fluid.

6. The apparatus as in claim 1, wherein said frame has a larger slider tube in sliding engagement with a smaller slider tube, and wherein a first grip configured for engaging the drum is attached to said larger slider tube and a second grip configured for engaging the drum is attached to said smaller slider tube; and
further comprising a clamp attached to said frame and configured for limiting sliding movement between said larger and smaller slider tubes.

7. An apparatus for piercing a drum plug of a drum, comprising:
a frame configured for engagement with a drum;
a cylinder mounted to said frame, said cylinder configured for actuation by a fluid;
a solid piercer in communication with said cylinder such that actuation of said cylinder causes said piercer to move, wherein said piercer is configured for puncturing the drum plug of the drum, said piercer defining a slot on an exterior surface of said piercer;
a collection tube urged towards the drum plug during actuation of said cylinder, wherein said collection tube defines an interior in communication with said slot on said piercer for the transport of gases from the drum, and wherein said collection tube is configured to remain on one side of the drum plug during puncturing of the drum plug by said piercer, wherein said piercer has a solid center, and wherein said exterior surface onto which said slot is defined directly faces an interior wall of said collection tube when said cylinder is in an unactuated state; and
a collection canister that is in fluid communication with the drum through said slot, said collection tube and a collection line attached to said collection tube, wherein the position of said collection line remains stationary with respect to said collection tube and the drum plug during movement of said piercer through the drum plug of the drum, and wherein the oases are moved through the collection tube.

8. The apparatus as in claim 7, wherein said collection tube surrounds at least a portion of said piercer when said cylinder is in the unactuated state, and wherein said collection tube defines a collection tube port.

9. The apparatus as in claim 8, wherein said collection canister is configured for receiving and storing gases for testing.

10. The apparatus as in claim 7, further comprising a ram disposed between and attached to both said cylinder and said piercer, wherein actuation of said cylinder urges said ram towards said collection tube.

11. The apparatus as in claim 7, further comprising a stack of disc springs positioned between said cylinder and said collection tube, wherein actuation of said cylinder causes compression of said disc springs.

12. The apparatus as in claim 7, further comprising a nylon washer located on an end of said collection tube, wherein said nylon washer forms a seal against the drum plug when said cylinder is actuated to urge said collection tube towards the drum plug during puncturing of the drum plug, and wherein said nylon washer is unsealed against the drum plug to allow gas in the drum to vent when force provided by said cylinder is relieved after puncturing the drum plug.

13. The apparatus as in claim 7, wherein:
said cylinder is a hydraulic cylinder and said fluid is a hydraulic fluid;
said frame has a larger slider tube in sliding engagement with a smaller slider tube, and wherein a first grip configured for engaging the drum is attached to said larger slider tube and a second grip configured for engaging the drum is attached to said smaller slider tube, and wherein said frame has a cylinder connector on said larger slider tube for mounting said cylinder to said larger slider tube; and
further comprising a clamp attached to said frame and configured for limiting sliding movement between said larger and smaller slider tubes.

14. A method of piercing a drum plug of a drum and collecting a gas sample therefrom, comprising the steps of:
attaching a frame to the drum such that a collection tube and a piercer carried by the frame are positioned over the drum plug of the drum, said piercer defining a slot on an exterior surface of said piercer;

actuating a cylinder such that said piercer is linearly driven through the drum plug of the drum, and such that said collection tube is urged against the exterior of the drum plug and forms a seal therewith, wherein said piercer has a solid center, and wherein said exterior surface onto which said slot is defined directly faces an interior wall of said collection tube when said cylinder is in an unactuated state; and collecting gas from the drum into a collection canister that is in fluid communication with the drum through said slot, said collection tube and a collection line attached to said collection tube, wherein the position of said collection line remains stationary with respect to said collection tube and the drum plug during movement of said piercer through the drum plug of the drum, and wherein the gas is moved through the collection tube.

15. The method as in claim 14, further comprising the step of venting the drum by reducing force on the collection tube from said cylinder such that said collection tube becomes unsealed with the drum plug.

16. The method as in claim 14, wherein the step of attaching includes sliding larger and smaller slider tubes with respect to one another until first and second grips carried by the slider tubes engage the drum, and wherein said step of attaching includes tightening a clamp to effect locking of said first and second grips onto the drum.

17. The method as in claim 14, further comprising the step of compressing a stack of disc springs positioned between said cylinder and said collection tube.

* * * * *